US008999943B2

(12) United States Patent
Corey et al.

(10) Patent No.: US 8,999,943 B2
(45) Date of Patent: Apr. 7, 2015

(54) ANTIGENE OLIGOMERS INHIBIT TRANSCRIPTION

(75) Inventors: David Reid Corey, Dallas, TX (US); Bethany Ann Janowski, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1399 days.

(21) Appl. No.: 11/376,483

(22) Filed: Mar. 14, 2006

(65) Prior Publication Data

US 2006/0205635 A1 Sep. 14, 2006

Related U.S. Application Data

(60) Provisional application No. 60/661,769, filed on Mar. 14, 2005.

(51) Int. Cl.
*C12N 15/11* (2006.01)
*C12N 15/113* (2010.01)

(52) U.S. Cl.
CPC .......... *C12N 15/113* (2013.01); *C12N 2310/11* (2013.01); *C12N 2310/14* (2013.01); *C12N 2310/3181* (2013.01); *C12N 2310/3233* (2013.01)

(58) Field of Classification Search
USPC ....................................................... 514/44 A
See application file for complete search history.

(56) References Cited

U.S. PATENT DOCUMENTS

| | | | | |
|---|---|---|---|---|
| 5,859,221 | A | 1/1999 | Cook et al. | 536/23.1 |
| 5,877,160 | A | 3/1999 | Harper et al. | |
| 6,506,559 | B1 | 1/2003 | Fire et al. | 435/6 |
| 6,673,611 | B2 | 1/2004 | Thompson et al. | 435/455 |
| 6,867,349 | B2 | 3/2005 | Ekker et al. | 800/21 |
| 2002/0078471 | A1 | 6/2002 | Ekker et al. | |
| 2003/0143732 | A1 | 7/2003 | Fosnaugh et al. | 514/44 |
| 2003/0165934 | A1 | 9/2003 | Elledge et al. | 435/6 |
| 2004/0259097 | A1 | 12/2004 | De Backer et al. | 435/6 |
| 2004/0259247 | A1* | 12/2004 | Tuschl et al. | 435/375 |
| 2005/0032733 | A1 | 2/2005 | McSwiggen et al. | 514/44 |
| 2005/0171039 | A1 | 8/2005 | McSwiggen et al. | 514/44 A |
| 2006/0205635 | A1 | 9/2006 | Corey et al. | 514/44 |
| 2007/0111963 | A1 | 5/2007 | Corey et al. | 514/44 |

FOREIGN PATENT DOCUMENTS

| | | |
|---|---|---|
| WO | WO 01/75164 | 10/2001 |
| WO | WO 01/83793 | 11/2001 |
| WO | WO 02/060919 | 8/2002 |
| WO | WO 03/070918 | 8/2003 |
| WO | WO 2006/113246 | 10/2006 |
| WO | WO 2006/130201 | 12/2006 |
| WO | WO 2007/086990 | 8/2007 |

OTHER PUBLICATIONS

Park et al. (Biochem. Biophys. Res. Comm. 2004; vol. 323, pp. 275-280).*
Keen et al. (Cancer 2003; vol. 97(S3), pp. 825-833).*
Kaihatsu, Recognition of Chromosomal DNA by PNAs, Chemistry & Biology, 2004, vol. 11, p. 749-758.
Affymetrix/Cold Spring Harbor Laboratory ENCODE Transcriptome Project, "Post-transcriptional processing generates a diversity of 5'-modified long and short RNAs," *Nature*, 457:1028-1032, 2009.
Braasch et al., "RNA interference in mammalian cells by chemically-modified RNA," *Biochemistry*, 42:7967-7975, 2003.
Check, "RNA interference: hitting the on switch," *Nature*, 448(7156):855-858, 2007.
Corey, "RNA learns from antisense," *Nat. Chem. Biol.*, 3:8-11, 2007.
Czauderna et al. "Structural variations and stabilising modifications of synthetic siRNAs in mammalian cells," *Nucleic Acids Res.*, 31(11):2705-2716, 2003.
Elmén et al., "Locked nucleic acid (LNA) mediated improvements in siRNA stability and functionality," *Nucleic Acids Res.*, 33(1):439-447, 2005.
Gingeras, "Origin of phenotypes: genes and transcripts," *Genome Res.*, 17:682-690, 2007.
Han et al., "Promoter-associated RNA is required for RNA-directed transcriptional gene silencing in human cells," *Proc. Natl. Acad. USA*, 104:12422-12427, 2007.
International Search Report and Written Opinion issued in International Application No. PCT/US2006/009776, mailed Sep. 5, 2006.
Janowski et al., "Activating gene expression in mammalian cells with promoter-targeted duplex RNAs," *Nat. Chem. Biol.*, 3:166-173, 2007.
Janowski et al., "Inhibiting gene expression at transcription start sites in chromosomal DNA with antigene RNAs," *Nature Chemical Biology*, 1:216-222, 2005.
Janowski et al., "Inhibiting transcription of chromosomal DNA with antigene peptide nucleic acids," *Nat Chem. Biol.*, 1(4):210-215, 2005.
Janowski et al., "Involvement of AGO1 and AGO2 in mammalian transcriptional silencing," *Nat. Struc. Mol. Biol.*, 13:787-792, 2006.
Kawasaki et al., "Induction of DNA methylation and gene silencing by short interfering RNAs in human cells," *Nature*, 431:211-217, 2004.
Kim et al., "Argonaute-1 directs siRNA-mediated transcriptional gene silencing in human cells," *Nat. Struct. Mol. Biol.*, 13:793-797, 2006.
Li et al., "Small dsRNAs induce transcriptional activation in human cells," *PNAS*, 103:17337-17342, 2006.
Liu et al., "Argonaute2 is the catalytic engine of mammalian RNAi," *Science*, 305:1437-1441, 2004.
Meister et al., "Human Argonaute2 mediates RNA cleavage targeted by miRNAs and siRNAs," *Mol. Cell.*, 15:185-197, 2004.

(Continued)

*Primary Examiner* — J. E. Angell
(74) *Attorney, Agent, or Firm* — Parker Highlander PLLC

(57) ABSTRACT

Transcription of a gene in a mammalian cell is methylase-independently inhibited by contacting the cell with a nucleic acid oligomer of 12-28 bases complementary for a partially single-stranded target genomic sequence of the gene.

20 Claims, No Drawings

(56) References Cited

OTHER PUBLICATIONS

Morris et al., "Small interfering RNA-induced transcriptional gene silencing in human cells," *Science*, 305:1289-1292, 2004.

Office Action issued in U.S. Appl. No. 11/599,566, mailed Feb. 24, 2009.

Office Action issued in U.S. Appl. No. 11/599,566, mailed Jul. 9, 2008.

Office Action issued in U.S. Appl. No. 11/599,566, mailed Sep. 30, 2008.

Paroo and Corey, "Challenges for RNAi in vivo," *Trends Biotechnol.*, 22:390-394, 2004.

Pulukuri and Rao, "Small interfering RNA directed reversal of urokinase plasminogen activator demethylation inhibits prostate tumor growth and metastasis," *Cancer Res.*, 67:6637-6646, 2007.

Riken Genome Exploration Research Group and Genome Science Group (Genome Network Project Core Group) and the FANTOM Consortium, "Antisense transcription in the mammalian transcriptome," *Science*, 309(5740):1564-1566, 2005.

Suzuki et al., "Prolonged transcriptional silencing and CpG methylation induced by siRNAs targeted to the HIV-1 promoter region," *J. RNAi Gene Silencing*, 1:66-78, 2005.

Takai and Jones, "Comprehensive analysis of CpG islands in human chromosomes 21 and 22," *Proc Natl Acad Sci USA*, 99:3740-3745, 2002.

Takai and Jones, "The CpG island searcher: a new WWW resource," *In Silico Biol.*, 3:235-240, 2003.

The ENCODE Project Consortium, "Identification and analysis of functional elements in 1% of the human genome by the ENCODE pilot project," *Nature*, 447:799-816, 2007.

The FANTOM Consortium, "The transcriptional landscape of the mammalian genome," *Science*, 309:1559-1563, 2005.

Ting et al., "Short double-stranded RNA induces transcriptional gene silencing in human cancer cells in the absence of DNA methylation," *Nature Genetics*, 37:906-910, 2005.

U.S. Appl. No. 12/246,421, entitled "Modulating Gene Expression with agRNA and Gapmers Targeting Antisense Transcripts," by Jacob C. Schwartz et al., filed Oct. 6, 2008.

U.S. Appl. No. 61/058,909, entitled "Endogenous Small RNA Targets Gene Promoters in Mammalian Cells," by David R. Corey et al., filed Jun. 4, 2008.

Wahlestedt, "Natural antisense and noncoding RNA transcripts as potential drug targets,", *Drug Discovery Today*, 11(11-12):503-508, 2006.

Zhang et al., "Reduction of liver Fas expression by an antisense oligonucleotide protects mice from fulminant hepatitis," *Nature Biotech.*, 18:862-867, 2000.

Zhang et al., "Regulation of endothelial nitric oxide synthase by small RNA," *Proc. Natl. Acad. Sci USA*, 102:16967-16972, 2005.

Beane et al., "Inhibiting gene expression with locked nucleic acids (LNAs) that target chromosomal DNA," *Biochemistry*, 46(25):7572-7580, 2007.

Janowski and Corey, "Inhibiting transcription of chromosomal DNA using antigene RNAs," Nucleic Acids Symposium Series, 49:367-368, 2005.

Katayama et al., "Antisense transcription in the mammalian transcriptome," *Science*, 309(5740):1564-1566, 2005.

Office Communication, issued in European Patent Application No. 08835168.9, dated Nov. 18, 2010.

Buskirk et al., "In vivo evolution of an RNA-based transcriptional activator," *Chem. Biol.*, 10:533-40, 2003 (Abstract).

Ferrandina et al., "Expression of cyclooxygenase-2 (COX-2), receptors for estrogen (ER), and progesterone (PR), p53, ki67, and neu protein in endometrial cancer," *Gynecol Oncol.*, 98:383-9, 2005 (Abstract).

Kuwabara et al., "A small modulatory dsRNA specifies the fate of adult neural stem cells," *Cell*, 116:779-793, 2004.

Leung and Whottaker, "RNA interference: from gene silencing to gene-specific therapeutics," *Pharmacol. Ther.*, 107:222-39, 2005 (Abstract).

Long-Cheng et al., "Small interfering RNA directed transcriptional activation in human cells," *PNAS*, 103:17337-42, 2006.

Office Action, issued in U.S. Appl. No. 11/599,566, mailed Aug. 5, 2009.

Schwartz et al., "Antisense transcripts are targets for activating small RNAs," *Nature Structural & Molecular Biology*, 15:842-8, 2008.

\* cited by examiner

SEQUENCE LISTING

```
<160> NUMBER OF SEQ ID NOS: 80

<210> SEQ ID NO 1
<211> LENGTH: 19
<212> TYPE: DNA
<213> ORGANISM: artificial
<220> FEATURE:
<223> OTHER INFORMATION: synthetic oligomer

<400> SEQUENCE: 1
ccagtccaca gctgtcact                                                  19

<210> SEQ ID NO 2
<211> LENGTH: 19
<212> TYPE: DNA
<213> ORGANISM: artificial
<220> FEATURE:
<223> OTHER INFORMATION: synthetic oligomer

<400> SEQUENCE: 2
tgtctggcca gtccacagc                                                  19

<210> SEQ ID NO 3
<211> LENGTH: 19
<212> TYPE: DNA
<213> ORGANISM: artificial
<220> FEATURE:
```

<223> OTHER INFORMATION: synthetic oligomer

<400> SEQUENCE: 3
tgagctgaag gcaaagggt                                             19

<210> SEQ ID NO 4
<211> LENGTH: 19
<212> TYPE: DNA
<213> ORGANISM: artificial
<220> FEATURE:
<223> OTHER INFORMATION: synthetic oligomer

<400> SEQUENCE: 4
tcatgactga gctgaaggc                                             19

<210> SEQ ID NO 5
<211> LENGTH: 19
<212> TYPE: DNA
<213> ORGANISM: artificial
<220> FEATURE:
<223> OTHER INFORMATION: synthetic oligomer

<400> SEQUENCE: 5
tcacgaccga gttgatggc                                             19

<210> SEQ ID NO 6
<211> LENGTH: 19
<212> TYPE: DNA
<213> ORGANISM: artificial
<220> FEATURE:
<223> OTHER INFORMATION: synthetic oligomer

<400> SEQUENCE: 6
cacgattttc tgcatgttt                                             19

<210> SEQ ID NO 7
<211> LENGTH: 19
<212> TYPE: DNA
<213> ORGANISM: artificial
<220> FEATURE:
<223> OTHER INFORMATION: synthetic oligomer

<400> SEQUENCE: 7
tgcccccaga catgctggc                                             19

<210> SEQ ID NO 8
<211> LENGTH: 19
<212> TYPE: DNA
<213> ORGANISM: artificial
<220> FEATURE:
<223> OTHER INFORMATION: synthetic oligomer

<400> SEQUENCE: 8
catgacgact ggactcccc                                             19

<210> SEQ ID NO 9
<211> LENGTH: 19
<212> TYPE: DNA
<213> ORGANISM: artificial
<220> FEATURE:
<223> OTHER INFORMATION: synthetic oligomer

<400> SEQUENCE: 9
cttgaccact gcactccgc                                             19

-continued

```
<210> SEQ ID NO 10
<211> LENGTH: 19
<212> TYPE: RNA
<213> ORGANISM: artificial
<220> FEATURE:
<223> OTHER INFORMATION: synthetic oligomer

<400> SEQUENCE: 10
augacugagc ugaaggcaa                                                  19

<210> SEQ ID NO 11
<211> LENGTH: 19
<212> TYPE: RNA
<213> ORGANISM: artificial
<220> FEATURE:
<223> OTHER INFORMATION: synthetic oligomer

<400> SEQUENCE: 11
ggggagucca gucgucaug                                                  19

<210> SEQ ID NO 12
<211> LENGTH: 19
<212> TYPE: RNA
<213> ORGANISM: artificial
<220> FEATURE:
<223> OTHER INFORMATION: synthetic oligomer

<400> SEQUENCE: 12
gcggagugca guggucaag                                                  19

<210> SEQ ID NO 13
<211> LENGTH: 19
<212> TYPE: RNA
<213> ORGANISM: artificial
<220> FEATURE:
<223> OTHER INFORMATION: synthetic oligomer

<400> SEQUENCE: 13
gguguugucc ccgcucaug                                                  19

<210> SEQ ID NO 14
<211> LENGTH: 19
<212> TYPE: RNA
<213> ORGANISM: artificial
<220> FEATURE:
<223> OTHER INFORMATION: synthetic oligomer

<400> SEQUENCE: 14
auggaagggc agcacaacu                                                  19

<210> SEQ ID NO 15
<211> LENGTH: 19
<212> TYPE: RNA
<213> ORGANISM: artificial
<220> FEATURE:
<223> OTHER INFORMATION: synthetic oligomer

<400> SEQUENCE: 15
ugucugggca guccacagc                                                  19

<210> SEQ ID NO 16
<211> LENGTH: 19
<212> TYPE: RNA
<213> ORGANISM: artificial
<220> FEATURE:
<223> OTHER INFORMATION: synthetic oligomer
```

<400> SEQUENCE: 16
ugucucgcca gucgacagc                                                19

<210> SEQ ID NO 17
<211> LENGTH: 19
<212> TYPE: RNA
<213> ORGANISM: artificial
<220> FEATURE:
<223> OTHER INFORMATION: synthetic oligomer

<400> SEQUENCE: 17
ucucugggca guccagagc                                                19

<210> SEQ ID NO 18
<211> LENGTH: 19
<212> TYPE: RNA
<213> ORGANISM: artificial
<220> FEATURE:
<223> OTHER INFORMATION: synthetic oligomer

<400> SEQUENCE: 18
ucucucgcca gugcacacc                                                19

<210> SEQ ID NO 19
<211> LENGTH: 19
<212> TYPE: RNA
<213> ORGANISM: artificial
<220> FEATURE:
<223> OTHER INFORMATION: synthetic oligomer

<400> SEQUENCE: 19
ucucucgcga guccacagc                                                19

<210> SEQ ID NO 20
<211> LENGTH: 19
<212> TYPE: RNA
<213> ORGANISM: artificial
<220> FEATURE:
<223> OTHER INFORMATION: synthetic oligomer

<400> SEQUENCE: 20
ccaguccaca gcugucacu                                                19

<210> SEQ ID NO 21
<211> LENGTH: 19
<212> TYPE: RNA
<213> ORGANISM: artificial
<220> FEATURE:
<223> OTHER INFORMATION: synthetic oligomer

<400> SEQUENCE: 21
cuggccaguc cacagcugu                                                19

<210> SEQ ID NO 22
<211> LENGTH: 19
<212> TYPE: RNA
<213> ORGANISM: artificial
<220> FEATURE:
<223> OTHER INFORMATION: synthetic oligomer

<400> SEQUENCE: 22
ucuggccagu ccacagcug                                                19

<210> SEQ ID NO 23
<211> LENGTH: 19

```
<212> TYPE: RNA
<213> ORGANISM: artificial
<220> FEATURE:
<223> OTHER INFORMATION: synthetic oligomer

<400> SEQUENCE: 23
gucuggccag uccacagcu                                                    19

<210> SEQ ID NO 24
<211> LENGTH: 19
<212> TYPE: RNA
<213> ORGANISM: artificial
<220> FEATURE:
<223> OTHER INFORMATION: synthetic oligomer

<400> SEQUENCE: 24
ugucuggcca guccacagc                                                    19

<210> SEQ ID NO 25
<211> LENGTH: 19
<212> TYPE: RNA
<213> ORGANISM: artificial
<220> FEATURE:
<223> OTHER INFORMATION: synthetic oligomer

<400> SEQUENCE: 25
cugucuggcc aguccacag                                                    19

<210> SEQ ID NO 26
<211> LENGTH: 19
<212> TYPE: RNA
<213> ORGANISM: artificial
<220> FEATURE:
<223> OTHER INFORMATION: synthetic oligomer

<400> SEQUENCE: 26
gcugucuggc caguccaca                                                    19

<210> SEQ ID NO 27
<211> LENGTH: 19
<212> TYPE: RNA
<213> ORGANISM: artificial
<220> FEATURE:
<223> OTHER INFORMATION: synthetic oligomer

<400> SEQUENCE: 27
agcugucugg ccaguccac                                                    19

<210> SEQ ID NO 28
<211> LENGTH: 19
<212> TYPE: RNA
<213> ORGANISM: artificial
<220> FEATURE:
<223> OTHER INFORMATION: synthetic oligomer

<400> SEQUENCE: 28
aagcugucug gccagucca                                                    19

<210> SEQ ID NO 29
<211> LENGTH: 19
<212> TYPE: RNA
<213> ORGANISM: artificial
<220> FEATURE:
<223> OTHER INFORMATION: synthetic oligomer

<400> SEQUENCE: 29
```
aaagcugucu ggccagucc                                           19

<210> SEQ ID NO 30
<211> LENGTH: 19
<212> TYPE: RNA
<213> ORGANISM: artificial
<220> FEATURE:
<223> OTHER INFORMATION: synthetic oligomer

<400> SEQUENCE: 30
guuagaaagc ugucuggcc                                           19

<210> SEQ ID NO 31
<211> LENGTH: 19
<212> TYPE: RNA
<213> ORGANISM: artificial
<220> FEATURE:
<223> OTHER INFORMATION: synthetic oligomer

<400> SEQUENCE: 31
guuguuagaa agcugucug                                           19

<210> SEQ ID NO 32
<211> LENGTH: 19
<212> TYPE: RNA
<213> ORGANISM: artificial
<220> FEATURE:
<223> OTHER INFORMATION: synthetic oligomer

<400> SEQUENCE: 32
cguuguuaga aagcugucu                                           19

<210> SEQ ID NO 33
<211> LENGTH: 19
<212> TYPE: RNA
<213> ORGANISM: artificial
<220> FEATURE:
<223> OTHER INFORMATION: synthetic oligomer

<400> SEQUENCE: 33
gcguuguuag aaagcuguc                                           19

<210> SEQ ID NO 34
<211> LENGTH: 19
<212> TYPE: RNA
<213> ORGANISM: artificial
<220> FEATURE:
<223> OTHER INFORMATION: synthetic oligomer

<400> SEQUENCE: 34
ggcguuguua gaaagcugu                                           19

<210> SEQ ID NO 35
<211> LENGTH: 19
<212> TYPE: RNA
<213> ORGANISM: artificial
<220> FEATURE:
<223> OTHER INFORMATION: synthetic oligomer

<400> SEQUENCE: 35
aggcguuguu agaaagcug                                           19

<210> SEQ ID NO 36
<211> LENGTH: 19
<212> TYPE: RNA
<213> ORGANISM: artificial

```
<220> FEATURE:
<223> OTHER INFORMATION: synthetic oligomer

<400> SEQUENCE: 36
aggaggcguu guuagaaag                                                    19

<210> SEQ ID NO 37
<211> LENGTH: 19
<212> TYPE: RNA
<213> ORGANISM: artificial
<220> FEATURE:
<223> OTHER INFORMATION: synthetic oligomer

<400> SEQUENCE: 37
agaggaggag gcguuguua                                                    19

<210> SEQ ID NO 38
<211> LENGTH: 19
<212> TYPE: RNA
<213> ORGANISM: artificial
<220> FEATURE:
<223> OTHER INFORMATION: synthetic oligomer

<400> SEQUENCE: 38
ucccuagagg aggaggcgu                                                    19

<210> SEQ ID NO 39
<211> LENGTH: 19
<212> TYPE: RNA
<213> ORGANISM: artificial
<220> FEATURE:
<223> OTHER INFORMATION: synthetic oligomer

<400> SEQUENCE: 39
gggccucccu agaggagga                                                    19

<210> SEQ ID NO 40
<211> LENGTH: 19
<212> TYPE: RNA
<213> ORGANISM: artificial
<220> FEATURE:
<223> OTHER INFORMATION: synthetic oligomer

<400> SEQUENCE: 40
gggcggggcc ucccuagag                                                    19

<210> SEQ ID NO 41
<211> LENGTH: 21
<212> TYPE: DNA
<213> ORGANISM: artificial
<220> FEATURE:
<223> OTHER INFORMATION: synthetic oligomer

<400> SEQUENCE: 41
tgtctggcca gtccacagct t                                                 21

<210> SEQ ID NO 42
<211> LENGTH: 19
<212> TYPE: DNA
<213> ORGANISM: artificial
<220> FEATURE:
<223> OTHER INFORMATION: synthetic oligomer

<400> SEQUENCE: 42
tgtctggcca gtccacagc                                                    19
```

```
<210> SEQ ID NO 43
<211> LENGTH: 19
<212> TYPE: RNA
<213> ORGANISM: artificial
<220> FEATURE:
<223> OTHER INFORMATION: synthetic oligomer

<400> SEQUENCE: 43
cucagauggg gaacucuca                                                19

<210> SEQ ID NO 44
<211> LENGTH: 19
<212> TYPE: RNA
<213> ORGANISM: artificial
<220> FEATURE:
<223> OTHER INFORMATION: synthetic oligomer

<400> SEQUENCE: 44 agaugggaa cucucaccc                                                 19

<210> SEQ ID NO 45
<211> LENGTH: 19
<212> TYPE: RNA
<213> ORGANISM: artificial
<220> FEATURE:
<223> OTHER INFORMATION: synthetic oligomer

<400> SEQUENCE: 45
gggaacucuc acccugccu                                                19

<210> SEQ ID NO 46
<211> LENGTH: 19
<212> TYPE: RNA
<213> ORGANISM: artificial
<220> FEATURE:
<223> OTHER INFORMATION: synthetic oligomer

<400> SEQUENCE: 46
uaggagucac cauggcaac                                                19

<210> SEQ ID NO 47
<211> LENGTH: 19
<212> TYPE: RNA
<213> ORGANISM: artificial
<220> FEATURE:
<223> OTHER INFORMATION: synthetic oligomer

<400> SEQUENCE: 47
guugccaugu ccuagugac                                                19

<210> SEQ ID NO 48
<211> LENGTH: 19
<212> TYPE: RNA
<213> ORGANISM: artificial
<220> FEATURE:
<223> OTHER INFORMATION: synthetic oligomer

<400> SEQUENCE: 48
caccucccag cgcccccuc                                                19

<210> SEQ ID NO 49
<211> LENGTH: 19
<212> TYPE: RNA
<213> ORGANISM: artificial
<220> FEATURE:
<223> OTHER INFORMATION: synthetic oligomer
```

```
<400> SEQUENCE: 49
ccaccuccca gcgccccu                                              19

<210> SEQ ID NO 50
<211> LENGTH: 19
<212> TYPE: RNA
<213> ORGANISM: artificial
<220> FEATURE:
<223> OTHER INFORMATION: synthetic oligomer

<400> SEQUENCE: 50
uccaccuccc agcgccccc                                             19

<210> SEQ ID NO 51
<211> LENGTH: 19
<212> TYPE: RNA
<213> ORGANISM: artificial
<220> FEATURE:
<223> OTHER INFORMATION: synthetic oligomer

<400> SEQUENCE: 51
ggggcgcugg gagguggag                                             19

<210> SEQ ID NO 52
<211> LENGTH: 19
<212> TYPE: RNA
<213> ORGANISM: artificial
<220> FEATURE:
<223> OTHER INFORMATION: synthetic oligomer

<400> SEQUENCE: 52
ucuccaccuc ccagcgccc                                             19

<210> SEQ ID NO 53
<211> LENGTH: 19
<212> TYPE: RNA
<213> ORGANISM: artificial
<220> FEATURE:
<223> OTHER INFORMATION: synthetic oligomer

<400> SEQUENCE: 53
cucuccaccu cccagcgcc                                             19

<210> SEQ ID NO 54
<211> LENGTH: 19
<212> TYPE: RNA
<213> ORGANISM: artificial
<220> FEATURE:
<223> OTHER INFORMATION: synthetic oligomer

<400> SEQUENCE: 54
gcucuccacc ucccagcgc                                             19

<210> SEQ ID NO 55
<211> LENGTH: 19
<212> TYPE: RNA
<213> ORGANISM: artificial
<220> FEATURE:
<223> OTHER INFORMATION: synthetic oligomer

<400> SEQUENCE: 55
ggugagaagc gcagaggcu                                             19

<210> SEQ ID NO 56
```

```
<211> LENGTH: 19
<212> TYPE: RNA
<213> ORGANISM: artificial
<220> FEATURE:
<223> OTHER INFORMATION: synthetic oligomer

<400> SEQUENCE: 56
cggugagaag cgcagaggc                                              19

<210> SEQ ID NO 57
<211> LENGTH: 19
<212> TYPE: RNA
<213> ORGANISM: artificial
<220> FEATURE:
<223> OTHER INFORMATION: synthetic oligomer

<400> SEQUENCE: 57
ccggugagaa gcgcagagg                                              19

<210> SEQ ID NO 58
<211> LENGTH: 19
<212> TYPE: RNA
<213> ORGANISM: artificial
<220> FEATURE:
<223> OTHER INFORMATION: synthetic oligomer

<400> SEQUENCE: 58
accggugaga agcgcagag                                              19

<210> SEQ ID NO 59
<211> LENGTH: 19
<212> TYPE: RNA
<213> ORGANISM: artificial
<220> FEATURE:
<223> OTHER INFORMATION: synthetic oligomer

<400> SEQUENCE: 59 cguuaccgg ugagaagcg                                               19

<210> SEQ ID NO 60
<211> LENGTH: 19
<212> TYPE: RNA
<213> ORGANISM: artificial
<220> FEATURE:
<223> OTHER INFORMATION: synthetic oligomer

<400> SEQUENCE: 60
accgcuguua ccggugaga                                              19

<210> SEQ ID NO 61
<211> LENGTH: 19
<212> TYPE: RNA
<213> ORGANISM: artificial
<220> FEATURE:
<223> OTHER INFORMATION: synthetic oligomer

<400> SEQUENCE: 61
cuuccaccgc uguuaccgg                                              19

<210> SEQ ID NO 62
<211> LENGTH: 19
<212> TYPE: RNA
<213> ORGANISM: artificial
<220> FEATURE:
<223> OTHER INFORMATION: synthetic oligomer

<400> SEQUENCE: 62
```

-continued gaucgcggag gcuuggggc					19

<210> SEQ ID NO 63
<211> LENGTH: 19
<212> TYPE: RNA
<213> ORGANISM: artificial
<220> FEATURE:
<223> OTHER INFORMATION: synthetic oligomer

<400> SEQUENCE: 63
ggaggaucgc ggaggcuug					19

<210> SEQ ID NO 64
<211> LENGTH: 19
<212> TYPE: RNA
<213> ORGANISM: artificial
<220> FEATURE:
<223> OTHER INFORMATION: synthetic oligomer

<400> SEQUENCE: 64
gggaggaucg cggaggcuu					19

<210> SEQ ID NO 65
<211> LENGTH: 19
<212> TYPE: RNA
<213> ORGANISM: artificial
<220> FEATURE:
<223> OTHER INFORMATION: synthetic oligomer

<400> SEQUENCE: 65
ggggaggauc gcggaggcu					19

<210> SEQ ID NO 66
<211> LENGTH: 19
<212> TYPE: RNA
<213> ORGANISM: artificial
<220> FEATURE:
<223> OTHER INFORMATION: synthetic oligomer

<400> SEQUENCE: 66
cggggaggau cgcggaggc					19

<210> SEQ ID NO 67
<211> LENGTH: 19
<212> TYPE: RNA
<213> ORGANISM: artificial
<220> FEATURE:
<223> OTHER INFORMATION: synthetic oligomer

<400> SEQUENCE: 67
gcggggagga ucgcggagg					19

<210> SEQ ID NO 68
<211> LENGTH: 19
<212> TYPE: RNA
<213> ORGANISM: artificial
<220> FEATURE:
<223> OTHER INFORMATION: synthetic oligomer

<400> SEQUENCE: 68
agcggggagg aucgcggag					19

<210> SEQ ID NO 69
<211> LENGTH: 19
<212> TYPE: RNA

```
<213> ORGANISM: artificial
<220> FEATURE:
<223> OTHER INFORMATION: synthetic oligomer

<400> SEQUENCE: 69
uagcggggag gaucgcgga                                               19

<210> SEQ ID NO 70
<211> LENGTH: 19
<212> TYPE: RNA
<213> ORGANISM: artificial
<220> FEATURE:
<223> OTHER INFORMATION: synthetic oligomer

<400> SEQUENCE: 70
guagcgggga ggaucgcgg                                               19

<210> SEQ ID NO 71
<211> LENGTH: 19
<212> TYPE: RNA
<213> ORGANISM: artificial
<220> FEATURE:
<223> OTHER INFORMATION: synthetic oligomer

<400> SEQUENCE: 71
gguagcgggg aggaucgcg                                               19

<210> SEQ ID NO 72
<211> LENGTH: 19
<212> TYPE: RNA
<213> ORGANISM: artificial
<220> FEATURE:
<223> OTHER INFORMATION: synthetic oligomer

<400> SEQUENCE: 72
ugguagcggg gaggaucgc                                               19

<210> SEQ ID NO 73
<211> LENGTH: 19
<212> TYPE: RNA
<213> ORGANISM: artificial
<220> FEATURE:
<223> OTHER INFORMATION: synthetic oligomer

<400> SEQUENCE: 73
ucggcuggua gcggggagg                                               19

<210> SEQ ID NO 74
<211> LENGTH: 19
<212> TYPE: RNA
<213> ORGANISM: artificial
<220> FEATURE:
<223> OTHER INFORMATION: synthetic oligomer

<400> SEQUENCE: 74
aaaagucggc ugguagcgg                                               19

<210> SEQ ID NO 75
<211> LENGTH: 19
<212> TYPE: RNA
<213> ORGANISM: artificial
<220> FEATURE:
<223> OTHER INFORMATION: synthetic oligomer

<400> SEQUENCE: 75
uaaaagucgg cugguagcg                                               19
```

```
<210> SEQ ID NO 76
<211> LENGTH: 19
<212> TYPE: RNA
<213> ORGANISM: artificial
<220> FEATURE:
<223> OTHER INFORMATION: synthetic oligomer

<400> SEQUENCE: 76
uuuuuaaaag ucggcuggu                                                  19

<210> SEQ ID NO 77
<211> LENGTH: 19
<212> TYPE: RNA
<213> ORGANISM: artificial
<220> FEATURE:
<223> OTHER INFORMATION: synthetic oligomer

<400> SEQUENCE: 77
uuuuuuuuuu aaaagucgg                                                  19

<210> SEQ ID NO 78
<211> LENGTH: 19
<212> TYPE: RNA
<213> ORGANISM: artificial
<220> FEATURE:
<223> OTHER INFORMATION: synthetic oligomer

<400> SEQUENCE: 78
cccccuuuuu uuuuuaaaa                                                  19

<210> SEQ ID NO 79
<211> LENGTH: 19
<212> TYPE: RNA
<213> ORGANISM: artificial
<220> FEATURE:
<223> OTHER INFORMATION: synthetic oligomer

<400> SEQUENCE: 79 cgccccccccc uuuuuuuu                                                  19

<210> SEQ ID NO 80
<211> LENGTH: 19
<212> TYPE: RNA
<213> ORGANISM: artificial
<220> FEATURE:
<223> OTHER INFORMATION: synthetic oligomer

<400> SEQUENCE: 80
caugcgcccc ccccuuuuu                                                  19
```

1

ANTIGENE OLIGOMERS INHIBIT TRANSCRIPTION

This is a continuation of Ser. No. 60/661,769, filed Mar 14, 2005.

This invention was made with Government support under grants awarded by the National Institutes of Health (NIGMS 60642 and 73042). The Government has certain rights in this invention.

BACKGROUND OF THE INVENTION

Sequence-selective compounds that target chromosomal DNA might be used to regulate gene expression, probe the structural and functional importance of target sequences, direct sequence-specific mutations, and induce gene corrections (1). Difficult challenges, however, confront any scheme for developing compounds that recognize chromosomal DNA.

Before a synthetic antigene agent can bind a target sequence within a chromosome, it must cross both the outer cell and nuclear membranes. These agents must compete with chromatin structure and bound proteins to recognize and bind specific sequences within chromosomal DNA. Once bound, antigene agents must resist displacement by polymerases, helicases, and other proteins that participate in promoter recognition and transcription.

Several approaches have been developed for recognition of chromosomal DNA inside cells. Oligonucleotides can bind to duplex DNA by Hoogsteen base-pairing in the major groove to form triple helices (2,3). Alternatively, synthetic pyrimidine polyamides can recognize DNA through binding in the minor groove (4,5). More recently, duplex RNA targeting CpG islands within promoter DNA has been reported to silence gene expression in mammalian cells by inducing methylation (6,7), although negative results have also been reported (16). RNA-directed methylation had been well-studied in plants (Matzke et al, 2004; Chan et al, 2004) and yeast (Sugiyama et al, 2004; Sigova et al, 2004; and Motamedi et al, 2004), but these two positive recent reports were the first indication that RNA could also recognize sequences within the chromosomal DNA of mammalian cells. However, efficiency inhibition required delivering the RNA using lentiviral transduction (7), or simultaneously targeting multiple (ten) genomic regions (6). A recent review (Kawasaki et al, 2005) discusses the mechanism and implications of methylase-dependent, chromosome-targeted RNA interference (RNAi). Another review (Paroo and Corey, 2004) summarizes challenges for RNAi in vivo.

Peptide nucleic acids (PNAs) are nonionic DNA mimics that offer advantages for recognition of duplex DNA because hybridization is not hindered by phosphate-phosphate repulsion (1,8). Applications for strand invasion by PNAs include: creation of artificial primosomes (9), inhibition of transcription (10), activation of transcription (11), and directed mutagenesis (12). Several references report inhibition of gene transcription in human cells using antigene PNAs to target chromosomal DNA including coding regions (Boffa et al, 1996) and enhancer regions (Cutrona et al, 2003) of the targeted genes. Antigene PNAs targeting coding regions have also been reported to inhibit gene transcription when injected into rats (McMahon et al, 2002; Tyler et al, 1999). Transcription of a DNA restriction fragment in vitro has been reported to promote PNA binding about 50 bp downstream from phage promoters (10). A recent review summarizes use of PNAs for recognition of chromosomal DNA, and suggests that partially single-stranded regions like non-B-type structures and the open complex of transcription initiation might be susceptible to binding synthetic oligomers (1).

Strand invasion by PNAs in cell-free systems is most efficient at sequences that are partially single-stranded (13,14). Assembly of RNA polymerase and transcription factors into the pre-initiation complex on DNA induces the formation of a structure known as the open complex that contains several bases of unwound single-stranded DNA (15,16). Working in a cell-free prokaryotic system, Sigman and coworkers demonstrated that this single-stranded region of DNA was accessible to binding by short RNAs and that transcription could be inhibited (17). Inhibition was almost completely abolished by oligomers of 5 bases, whereas 8-mer sequences were much less effective, and there was no inhibition with 11-mer sequences. The authors concluded that RNA polymerase enforces rigid length and position constraints on open complex-targeted oligoribonucleotides.

SUMMARY OF THE INVENTION

One aspect of the invention is a method of methylase-independently inhibiting transcription of a gene in a mammalian cell (inhibiting transcription independent of DNA methylation), the method comprising the steps of: contacting the cell with a nucleic acid oligomer of 12-28 bases complementary to a partially single-stranded target genomic sequence of the gene, whereby the transcription of the gene is subject to a resultant methylase-independent inhibition; and detecting the resultant methylase-independent inhibition.

In one embodiment, the target genomic sequence is selected from the group consisting of an AT-rich sequence, a cruciform loop, a G-quadruplex, a nuclease hypersensitive element (NHE), and an open complex region located between nucleotides −50 to +25 from the gene's transcription start site.

In one embodiment the target genomic sequence is an open complex region located between or including, nucleotides −30 to +17, −15 to +10, or −9 to +2 from the transcription start site. In one embodiment, the target genomic sequence includes the transcription start site.

In one embodiment of the invention, the oligomer is selected from the group consisting of a double-stranded RNA, a DNA, a peptide nucleic acid, and a morpholino.

In one embodiment of the invention, the oligomer is a double-stranded RNA, and the target genomic sequence is not within a CpG island. In a further embodiment, the oligomer is a double-stranded RNA, and the target genomic sequence does not include a CG dinucleotide.

In a preferred embodiment of the invention, the oligomer is a double-stranded RNA of 18-25 bases.

In one embodiment of the invention, the oligomer is double-stranded RNA comprising a nucleotide having a 2' chemical modification.

In a further embodiment of the invention, the oligomer is double-stranded RNA comprising a serum stability-enhancing chemical modification selected from the group consisting of a phosphorothioate internucleotide linkage, a 2'-O-methyl ribonucleotide, a 2'-deoxy-2'-fluoro ribonucleotide, a 2'-deoxy ribonucleotide, a universal base nucleotide, a 5-C-methyl nucleotide, an inverted deoxyabasic residue incorporation, and a locked nucleic acids.

In one embodiment of the invention, the cell is a cultured cell in vitro.

In another embodiment of the invention, the cell is in situ in a host.

In a further embodiment of the invention, the cell is a cultured cell in vitro, the oligomer is a double-stranded RNA of 18-25 bases, and the cell is contacted with a composition comprising the oligomer and a cationic lipid.

In another embodiment of the invention, the cell is in situ in a host, the oligomer is a double-stranded RNA of 18-25 bases, and the cell is contacted with a composition consisting essentially of the oligomer.

In one embodiment of the invention, the contacting step is free of viral transduction, In a further embodiment of the invention, the contacting step is free of viral transduction, and the cell is contacted with a composition consisting essentially of the oligomer.

In a preferred embodiment of the invention, the contacting step is free of viral transduction, and the inhibition is at least 90%.

In a further embodiment of the invention, the oligomer is a double-stranded RNA of 18-25 bases, the inhibition is at least 90%, and a single sequence of the gene is targeted.

In another embodiment, the contacting step is free of viral transduction, and the oligomer is not attached to a nuclear localization peptide.

In one embodiment of the invention, the cell is contacted with a nanomolar concentration of the oligomer.

In another embodiment of the invention, the cell is a breast carcinoma cell and the gene is the human progesterone receptor or the human androgen receptor.

Another aspect of the invention is a nucleic acid oligomer for methylase-independent inhibition of transcription of a human progesterone receptor gene, the oligomer comprising a nucleotide sequence of 12-28 bases complementary to a target sequence located between nucleotides −50 to +25 of the transcription start site of the gene. In a further embodiment, the oligomer is selected from the group consisting of RNA, DNA, peptide nucleic acid and morpholino.

In a preferred embodiment, the oligomer is a double-stranded RNA of 18-25 bases comprising a nucleotide sequence selected from the group consisting of SEQ ID NO:20-28, 32, 33, 35, 36, 38, and 40.

Another aspect of the invention is a nucleic acid oligomer for methylase-independent inhibition of transcription of a human androgen receptor gene, the oligomer comprising a nucleotide sequence of 12-28 bases complementary to a target sequence located between nucleotides −50 to +25 of the transcription start site of the gene. In a further embodiment, the oligomer is selected from the group consisting of RNA, DNA, peptide nucleic acid, and morpholino.

In a preferred embodiment, the oligomer is a double-stranded RNA of 18-25 bases comprising a nucleotide sequence selected from the group consisting of SEQ ID NO:48-51, 53, and 54.

Another aspect of the invention is a nucleic acid oligomer for methylase-independent inhibition of transcription of a human vascular endothelial growth factor gene, the oligomer comprising a nucleotide sequence of 12-28 bases complementary to a target sequence located between nucleotides −50 to +25 of the transcription start site of the gene.

In a further embodiment, the oligomer is selected from the group consisting of RNA, DNA, peptide nucleic acid, and morpholino.

In a preferred embodiment, the oligomer is a double-stranded RNA of 18-25 bases.

Another aspect of the invention is a method of doing business comprising promoting, marketing, selling or licensing a subject invention.

DETAILED DESCRIPTION OF SPECIFIC EMBODIMENTS OF THE INVENTION

The invention provides a method for methylase-independently inhibiting transcription of a gene in a mammalian cell. The method comprises the steps of contacting the cell with a nucleic acid oligomer of 12-28 bases complementary to a partially single-stranded target genomic sequence of the gene, whereby the transcription of the gene is subject to a resultant methylase-independent inhibition, and detecting the resultant methylase-independent inhibition.

The target genomic sequence is partially single-stranded. The single-strandedness is a consequence of and/or predictable from the sequence, and thus is sequence-dependent, in contrast to sequence-independent single stranded sequences that may transiently occur in genomic DNA, for example, as the result of the migrating transcription bubble which forms when RNA polymerase releases from the core promoter, initiating transcription elongation. Preferred sequence-dependent, partially single-stranded target genomic sequences include non-B-DNA structures, AT-rich sequences, cruciform loops, G-quadruplexes, nuclease hypersensitive elements (NHE), open complex regions located between nucleotides −50 to +25 from the transcription start site, etc.

Preferred AT-rich sequences are found in stretches of DNA where local melting occurs, such as the promoters of genes where protein machinery must gain access to single-stranded regions, and preferably comprise the TATA box of the gene, and/or at least 60% or 70% A+T.

Preferred cruciform structures are formed from palindromic genomic sequences forming a hairpin structure on each strand, wherein the repeated sequences are separated by a stretch of non-palindromic DNA providing a single-stranded loop at the end of each of the hairpins of the cruciform. Such cruciform structures have been implicated in control of transcription, and provide a targetable partially single-stranded structure.

Preferred G-quadruplex structures are identified in promoter regions of mammalian genes and are implicated in transcription regulation. For example the nuclease hypersensitivity element III of the c-mMYC oncogene promoter is involved in controlling transcription and comprises a pyrimidine-rich and purine-rich sequences on the coding and non-coding strands, respectively, that can adopt I-motif and G-quadruplex structures, respectively. Stabilization of the G-quadruplex has been shown to lead to repression of c-MYC (see e.g. Siddiqui-Jain, 2002).

Preferred open complexes are located between about nucleotides −50 to +25 from the gene's transcription start site. Formation of the open complex is preceded by the recruitment of RNA polymerase and transcription factors to the gene's core promoter, forming a preinitiation complex. Next, a conformational change occurs in which 11-15 base pairs of DNA surrounding the transcriptional start site are melted and a single-stranded portion of the template strand of the promoter is positioned within the active site cleft of RNA polymerase to form the open complex (see e.g. Hahn, 2004). In certain preferred embodiments of the method, the target genomic sequence is an open complex region located on the template strand between nucleotides −30 to +17 from the transcription start site of the gene. In another embodiment, the target sequence is located between nucleotides −15 to +10 from the transcription start site. In a further embodiment, the target sequence includes nucleotides −9 to +2 from the transcription start site. In certain preferred embodiments, the target genomic sequence includes the transcription start site. In other embodiments, the target sequence does not include any sequence downstream from the transcription start, e.g. the sequence is located between nucleotides −50 to +1. In one embodiment, the target sequence is selected so as to inhibit transcription prior to the stage at which RNA polymerase would otherwise release from the core promoter and enter the stage of transcription elongation.

The nucleic acid oligomer is of a sequence and length sufficient to effect the requisite transcription inhibition. As used herein, the singular forms "a," "an," and "the," refer to both the singular as well as plural, unless the context clearly indicates otherwise. For example, the term "an oligomer" includes single or plural oligomers and can be considered equivalent to the phrase "at least one oligomer." Suitable oligomers are typically 12-28 bases in length, and are complementary to the target sequence (i.e. Watson-Crick binding complementarity). The oligomer may comprise any nucleic acid, modified nucleic acid, or nucleic acid mimic that can recognize DNA by Watson-Crick base-pairing. Mismatches between the oligomer and the target sequence, particularly more than one mis-match, often diminish the efficacy of transcription inhibition (see e.g., Example 1, Table 1). The oligomer may be single-stranded or double-stranded (i.e. a duplex). In the case of duplex oligomers, a first strand is complementary to the genomic target sequence, and the second strand is complementary to the first strand. In certain embodiments where the oligomer is a duplex, the target region is a non-coding region of the gene, resulting in antigene transcription inhibition and not antisense inhibition of mRNA. The oligomer may target homopyrimidine sequences, homopyrimidine sequences, or mixed purine/pyrimidine sequences. A mixed purine/pyrimidine sequence contains at least one purine (the rest being pyrimidines) or at least one pyrimidine (the rest being purines). A variety of oligomers are known in the art that are capable of Watson-Crick base-pairing. In certain embodiments, the oligomer is selected from a double-stranded RNA, a DNA, a peptide nucleic acid, and a morpholino.

Double-stranded (ds) RNAs are particularly preferred oligomers because they are relatively easy to synthesize, and have been used in human clinical trials. Preferred dsRNAs have 18-25 bases complementary to the target sequence, and optionally have 3' di-or tri-nucleotide overhangs on each strand. Methods for preparing dsRNA and delivering them to cells are well-known in the art (see e.g. Elbashir et al, 2001; WO/017164 to Tuschl et al; and U.S. Pat. No. 6,506,559 to Fire et al). Custom-made dsRNAs are also commercially available (e.g. Ambion Inc., Austin, Tex). The dsRNA used in the method of the invention may be chemically modified to enhance a desired property of the molecule. A broad spectrum of chemical modifications can be made to duplex RNA, without negatively impacting the inhibitory properties. In one embodiment, the dsRNA comprises one or more nucleotides having a 2' modification, and may be entirely 2'-substituted. A variety of 2' modifications are known in the art (see e.g. U.S. Pat. No. 5,859,221 to Cook et al.; U.S. Pat. No. 6,673,611 to Thompson et al; and Czaudema et al, 2003). A preferred chemical modification enhances serum stability and increases the half-life of dsRNA when administered in vivo. Examples of serum stability-enhancing chemical modifications include phosphorothioate intenucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation (see e.g. US Patent Publication No. 20050032733 to McSwiggen et al). The dsRNA may optionally contain locked nucleic acids (LNAs) to improve stability and increase nuclease resistance (see e.g. Elmen et al, 2005; and Braasch et al, 2003).

Methylase-dependent inhibition of transcription using antigene dsRNA targeting CpG islands has been described (6,7). However, the inhibition achieved by the method of the present invention is methylase-independent, wherein inhibition is effected independent of, and without requiring effective methylation (e.g. transcription inhibition still occurs if the cell is contacted with the oligomer in the presence of a methylase inhibitor); thus the target genomic sequence need not be located in a CpG island region, greatly increasing the utility of dsRNA for antigene applications. In a particular embodiment of the invention, the genomic target sequence is not contained within a CpG island. Algorithms for identifying CpG islands in genomic sequences are known (e.g see Takai and Jones, 2002; and Takai and Jones 2003). In another embodiment of the invention, the oligomer is a double-stranded RNA, and the target genomic sequence does not include a CG dinucleotide.

Peptide nucleic acids (PNAs) are also preferred oligomers for use in the method of the invention. Various PNA configurations are known in the art. For example, the PNA oligomer may be homopyrimidine, optionally prepared as a bisPNA, where one PNA oligomer binds the target via Watson-Crick base pairing, and a second oligomer binds via Hoogsteen recognition (see e.g. Nielsen, 2004); homopurine, optionally substituting one or more adenines with diaminopurine (see e.g. Haaima et al, 1997); or mixed purine/pyrimidine, optionally configured to form a tail-clamp at the target sequence (see e.g. Kaihatsu et al, 2003). In a preferred embodiment, the PNA is single-stranded mixed purine/pyrimidine.

DNA oligomers can also be used in the method of the invention. However, unmodified oligodeoxynucleotides are subject to rapid degradation by nucleases. Therefore, when DNA oligomers are used, they preferably have chemical modifications to increase nuclease resistance. A variety of chemical modifications to increase nuclease resistance are known in the art. The simplest and most widely used modification is the phosphorothioate (PS) modification, in which a sulfur atom replaces a non-bridging oxygen in the oligophosphate backbone. DNA oligomers are commercially available through numerous vendors (e.g. Integrated DNA Technologies, Coralville, Iowa).

Other types of oligomers that can be used include morpholino oligomers (see e.g. Summerton and Weller, 1997) and LNAs (see e.g. Wahlestedt et al, 2000).

The mammalian cell that is contacted with the oligomer can be in vitro (e.g. a cultured cell), or in situ in a host. Examples of cultured cells include primary cells, cancer cells (e.g. from cell lines), adult or embryonic stem cells, neural cells, fibroblasts, myocytes, etc. The cell can be from any mammal. In one embodiment, the cell is a human cell in vitro. In a further embodiment, the cell is a breast carcinoma cell and the gene is the human progesterone receptor or the human androgen receptor. Cultured human cells commonly used to test putative therapeutics for human diseases or disorders can be used to screen oligomers that target partially single-stranded genomic sequences of genes for therapeutic affect (e.g. induction of apoptosis, cessation of proliferation in cancer cells, etc.). When the cell is in situ, the host may be any mammal, and in certain preferred embodiments is a human, or an animal model used in the study of human diseases or disorders (e.g. rodent, canine, porcine, etc. animal models).

In the contacting step, the methods used to deliver the oligomer to the cell can vary depending on the oligomer used and whether the cell is in vitro or in vivo. For cells in vitro, delivery can be accomplished by direct injection into cells. When microinjection is not an option, delivery can be enhanced in some cases by using hydrophobic or cationic carriers such as Lipofectamine™ (Invitrogen, Carlsbad, Calif.). In one embodiment of the invention, the cell is a cultured cell in vitro, the oligomer is a double-stranded RNA of 18-25 bases, and the cell is contacted with a composition comprising the oligomer and a cationic lipid. PNA oligomers can be introduced into cells in vitro by complexing them with partially complementary DNA oligonucleotides and cationic lipid (21-25). The lipid promotes internalization of the DNA, while the PNA enters as cargo and is subsequently released. Peptides such as penetratin, transportan, Tat peptide, nuclear localization signal (NLS), and others, can be attached to the oligomer to promote cellular uptake (see e.g., Nielsen, 2004; Kaihatsu et al, 2003; Kaihatsu, et al, 2004; and ref. 7). Alternatively, the cells can be permeabilized with a permeabilization agent such as lysolecithin, and then contacted with the oligomer. Viral transduction can be used to deliver oligomers to cells in vitro (e.g. lentiviral transduction, see e.g. ref 7). However, in certain embodiments of the invention, it is preferred that the contacting step is free of viral transduction. In a further preferred embodiment, the contacting step is free of viral transduction, and the oligomer is not attached to a nuclear localization peptide.

For cells in situ, cationic lipids (see e.g. Hassani et al, 2004) and polymers such as polyethylenimine (see e.g. Urban-Klein, 2005) have been used to facilitate oligomer delivery. Compositions consisting essentially of the oligomer (in a carrier solution) can be directly injected into the host (see e.g. Tyler et al, 1999; McMahon et al, 2002). In a preferred embodiment of the invention, the cell is in situ in a host, the oligomer is a double-stranded RNA of 18-25 bases, and the cell is contacted with a composition consisting essentially of the oligomer. In vivo applications of duplex RNAs are reviewed in Paroo and Corey, Highly efficient transcription inhibition can be achieved using the methods of the invention. Target sequences can be selected to achieve varying degrees of inhibition, e.g. at least 50%, 60%, 70%, 80%, 90%, 95%, 98%, or 99% inhibition; even complete inhibition (i.e. 100%) can be achieved. The inhibition is independent of mRNA inhibition. In preferred embodiments, the inhibition is at least 90%. Efficient inhibition can be achieved without viral transduction, and thus, in some preferred embodiments of the invention, the contacting step is free of viral transduction, and the inhibition is at least 90%. While multiple single-stranded regions of the gene can be targeted, highly efficient inhibition can be achieved with dsRNA targeting just a single sequence of the gene, in contrast to prior methods where multiple targets were required to achieve a high degree of inhibition (see e.g. ref 6). In one preferred embodiment of invention, the oligomer is a double-stranded RNA of 18-25 bases, the inhibition is at least 90%, and a single sequence of the gene is targeted. Highly efficient inhibition can be achieved using nanomolar (submicromolar) concentrations of the oligomer. It is typically preferred to use the lowest concentration possible to achieve the desired degree of inhibition, e.g. oligomer concentrations in the 1-100 nM range are preferred; more preferably, the concentration is in the 1-50 nM, 1-25 nM, or 1-10 nM range.

In the detecting step of the method, methylase-independent inhibition, resulting from the oligomer contacting the cell, is detected. For cells in vitro, transcription inhibition of a gene can be detected by measuring a decrease in the level of the gene's mRNA transcript or corresponding encoded protein compared to controls. Whether a resultant inhibition is methylase-independent can be determined in control studies where the ability of the oligomer to inhibit transcription in the presence of a methylase inhibitor such as 5-azacytidine (5-azaC) or 5 aza-2'-deoxycytidine (5-aza-dC). Methylation may also be detected directly, e.g. by sequencing cloned PCR products. For example, to further confirm that DNA methylation was not involved in the gene silencing of our examples, we sequenced the regions surrounding the AR, hPR-B, and hPR-A transcription start sites after treatment with agRNAs. Between five and fifteen cloned PCR products were sequenced for each sample of sodium bisulfite-treated DNA, and no methylation was observed.

Alternatively, the detection step may comprise inferentially determining that methylase-inhibition has resulted. For example, decreased transcription compared to controls may be detected, and it may be inferred that the transcription is methylase-independent because the target sequence is not located in a CpG island. For cells in situ, the detection step may comprise measuring a decrease in the level of transcription of the targeted gene, or a decrease in the level of encoded protein. Alternatively, resultant inhibition may be inferred based on phenotypic changes that are indicative of inhibition of the targeted gene. Further, that a resultant inhibition is methylase-independent may be inferred from knowledge that the targeted sequence is not located in a CpG island, or that prior in vitro studies show that transcription inhibition is methylase-independent.

In another aspect of the invention, provided are nucleic acid oligomers for methylase-independent inhibition of gene transcription. The oligomer comprises a nucleotide sequence of 12-28 bases complementary to a target sequence located between nucleotides −50 to +25 of the transcription start site of the gene. In one embodiment, the gene is the human progesterone receptor gene, the human androgen receptor gene, or the human vascular endothelial growth factor gene. In further embodiments, the oligomer is RNA, DNA, peptide nucleic acid or morpholino. In one embodiment, the nucleic acid oligomer is a double-stranded RNA of 18-25 bases. In a specific embodiment, the gene is the human progesterone receptor gene, and the double-stranded RNA comprises a nucleotide sequence selected from SEQ ID NOs 20-25, 27, 28, 33, 35, 39, and 49. In another embodiment, the gene is the human androgen receptor gene, and the double-stranded RNA comprises a nucleotide sequence selected from SEQ ID NO:48-51, 53, and 54.

In a further aspect of the invention, the invention provides a method of doing business comprising promoting, marketing, selling or licensing any of the aforementioned inventions.

EXAMPLE 1

Inhibition of Human Progesterone Receptor (hPR) Expression by Antigene PNA (agPNA) Oligomers Targeting the Open Complex in Chromosomal DNA Cell Culture. T47D breast cancer cells were obtained from the American Type Cell Culture Collection (ATCC) and maintained at 37° C. and 5% $CO_2$ in RPMI media (ATCC) supplemented with 10% (v/v) heat-inactivated (56° C., 1 hr) fetal bovine serum (Gemini Bio-products), 0.5% non-essential amino acids (Sigma), 0.4 units/mL bovine insulin (Sigma) and 100 units/ml penicillin and 0.1 mg/ml streptomycin (Sigma).

Lipid-Mediated Transfection of PNA/DNA and siRNA Duplexes. PNAs and DNAs were obtained as described (21-25). RNA was synthesized by the Center for Biomedical Inventions at The University of Texas Southwestern Medical Center.

Two days before transfection (day 2), T47D cells were plated at 80,000 cells per well in 6-well plates (Costar). On the day of transfection (day 0) duplexes (200 nM) and Oligofectamine (9 µL per well, Invitrogen) were diluted in Optimem (Invitrogen) according to the manufacturers' instructions. Media was changed 24 h later (day 1). For antisense PNAs or siRNAs cells were harvested on day 5. For agPNAs, on day 3 cells were passaged 1:4 into new 6-well plates. Cells were transfected a second time on day 5. Cells were harvested day 8 or as indicated. hPR protein levels were evaluated by Western analysis using anti-hPR antibody (Cell Signaling Technologies).

RNA Analysis. Total RNA from treated T47D cells was extracted using trizol (TRIzol, Invitrogen) (26). RNA was treated with deoxyribonuclease to remove contaminating DNA, and 4 µg were reverse transcribed by random primers using Superscript II RNase H-reverse transcriptase (Invitrogen).

Microscopy. Cells were imaged by confocal microscopy using a Zeiss Axiovert 200 M inverted transmitted light microscope (Carl Zeiss Microimaging). T47D cells transfected with siRNAs were seeded at 20,000 cells per well in Lab-Tek 4-well chambered coverglass slides (Nalgene Nunc International) at day-2. Cells were transfected with siRNA on day 0 and imaged on day 5. Cells were transfected with agPNA as described above, transferred to 4-WELL slides on day 3, transfected with PNA a second time on day 5, and harvested on day 8.

Approximations of cell height were made using the Zeiss Axi overt Microscope which has the ability to track distances in the Z-plane using an automated program. Individual cells were chosen for observation and then the microscope was underfocused until no part of the individual cell is in focus. The underfocus position in the Z-plane is noted and then the focal plane is moved upward through the cell until it is completely out of focus. The overfocus position is noted and a crude estimate of the height (Zdimension) of the cell can be calculated.

Cellular Uptake of Biologically Active PNAs. We introduced PNAs into cells by complexing them with partially complementary DNA oligonucleotides and cationic lipid (21-25). The lipid promotes internalization of the DNA, while the PNA enters as cargo and is subsequently released.

Using this method we have inhibited the ribonucleoprotein telomerase by targeting its RNA component and caused telomeres to shorten (22). We have also demonstrated that antisense PNAs targeting MRNA can inhibit gene expression (21,23-25). Active antisense PNAs can be targeted to the 5' terminus of the untranslated region (23), to sequences within an internal ribosome entry site (IRES) (25), or to sequences within the coding region of mRNA (24).

Target Sequences for agPNAs. We chose the gene encoding the human progesterone receptor (hPR) as a target. Two major isoforms, hPR-B and hPR-A, are expressed under the control of two different promoters, each encoding a separate transcript (18,19). The transcription start site of hPR-B is upstream from the start site of hPR-A. This order is important for the experiments that we describe here because the target sequences for agPNAs within the transcription start site of hPR-B are approximately 760 bases upstream from the start site of hPR-A and play no obvious role in expression of hPR-A. hPR plays an important role in normal physiologic processes and disease (20).

To determine whether PNAs could act as antigene agents inside cells we synthesized and tested nineteen base PNAs P1-P4 as shown in Table 1. The agPNAs are listed N to C termini and contain C— and N-terminal lysines. Mismatched (mm) bases are underlined. Human caveolin-1 is designated hCav. Only one strand (5' to 3') of each siRNA is shown. Additionally, the siRNAs had 3'-dithymidine overhangs on each strand. Sense PNAs are complementary to the template strand of chromosomal DNA; antisense PNAs are complementary to the transcribed mRNA.

TABLE 1

| PNA ID | Sequence | Target site |
|---|---|---|
| agPNAS targeting the hPR-B promoter and start site | | |
| P1 | CCAGTCCACAGCTGTCACT (SEQ ID NO: 1) | -2/+17 (Sense) |
| P2 | TGTCTGGCCAGTCCACAGC (SEQ ID NO: 2) | -9/+10 (Sense) |
| agPNAs targeting the hPR-A promoter and start site | | |
| P3 | TGAGCTGAAGGCAAAGGGT (SEQ ID NO: 3) | -2/+17 (Sense) |
| P4 | TCATGACTGAGCTGAAGGC (SEQ ID NO: 4) | -9/+10 (Sense) |
| P4 mm | TCACGACCGAGTTGATGGC (SEQ ID NO: 5) | -9/+10 (Sense) |
| Control PNAS that do not target hPR | | |
| P5 | CACGATTTTCTGCATGTTT (SEQ ID NO: 6) | Luciferase (23) |
| P6 | TGCCCCCAGACATGCTGGC (SEQ ID NO: 7) | hCav (24) |
| Antisense PNAs targeting hPR-B mRNA | | |
| P7 | CATGACGACTGGACTCCCC (SEQ ID NO: 8) | (Antisense) |
| P7 mm | CTTGACCACTGCACTCCGC (SEQ ID NO: 9) | (Antisense) |
| sIRNAs | | |
| S1 | AUGACUGAGCUGAAGGCAA (SEQ ID NO: 10) | hPR-B only |
| S2 | GGGGAGUCCAGUCGUCAUG (SEQ ID NO: 11) | hPR-B only |
| S2 mm | GCGGAGUGCAGUGGUCAAG (SEQ ID NO: 12) | hPR-B only |
| S3 | GGUGUUGUCCCCGCUCAUG (SEQ ID NO: 13) | hPR-B/A |
| S4 | AUGGAAGGGCAGCACAACU (SEQ ID NO: 14) | hPR-B/A |

PNAs P1 and P2 were targeted to the transcription start site of hPR-B and PNAs P3 and P4 were targeted to the transcription start site of hPR-A. hPR is transcribed by polymerase II and the open complex is predicted to contain single-stranded DNA from nucleotides −9 to +2 (15,16). It is important to note that P1-P4 were targeted to the template strand of the DNA. Therefore, P1-P4 are not complementary to the mRNA encoding hPR, and would not be expected to inhibit hPR expression by an antisense mechanism.

Inhibition of hPR Expression by agPNAs. We transfected PNAs P1-P4 into cells at a concentration of 200 nm and measured their ability to inhibit hPR protein expression by Western analysis. We observed that agPNAs P1-P4 inhibited hPR expression and reduced the levels of both hPR-B and hPR-A isoforms. Levels of inhibition varied among experiments, but hPR levels were typically reduced by 75-95%. This inhibition of hPR provides evidence that agPNAs can bind chromosomal DNA inside cells and block transcription. We were surprised that agPNAs P1 and P2 inhibited expression of both hPR-B and hPR-A because the target sequences for agPNAs P1 and P2 are not contained within the promoter or coding region of hPR-A. The fact that hPR-A expression is reduced by agPNAs that target sequences found only within hPR-B indicates that reduced expression of hPR-A is linked to reduced levels of hPR-B.

The observation that agPNAs P3 and P4 block expression of both isoforms is less surprising because P3 and P4 target sequences are also within the coding region for hPR-B. During transcription RNA polymerase forms a transcription bubble that contains single-stranded DNA. It is possible that P3 and P4 are binding to accessible target DNA sequences as the transcription bubble proceeds along the gene during transcription of hPR-B. Nielsen has reported this mechanism for inhibition for transcription by PNAs in cell free systems (10). Alternatively, PNAs may bind at the hPR-A start site prior to the initiation of transcription from the hPR-B promoter and may act as roadblocks to stop further transcription by polymerase. In either case, binding of agPNAs would block the ability of the RNA polymerase to transcribe a full-length hPR-B transcript and inhibit formation of the preinitiation complex at the hPR-A promoter.

Experiments that describe the effects of antisense oligonucleotides, PNAs, or siRNAs must be well-controlled to support the conclusion that observed phenotypes are due to binding the intended target. To demonstrate that inhibition was due to recognition of the target chromosomal sequences by P1-P4, we performed several control experiments. Mismatch-containing PNA P4 mm, PNA P5 that was complementary to luciferase mRNA (23), and PNA P6 that was complementary to caveolin-1 mRNA (24) did not inhibit hPR expression. The observed inhibition of hPR gene expression by four agPNAs (P1-P4) directed to the template DNA strand, and the lack of inhibition by three PNAs (P5-P7) that are not complementary to hPR indicates that the inhibition of hPR expression we observe is due to recognition of their intended chromosomal targets by agPNAs P1-P4. As noted above, the PNAs were not complementary to mRNA and were not expected to inhibit expression by an antisense mechanism.

Treatment with agPNAs Reduces Levels of hPR mRNA. To further support the conclusion that agPNAs P1-P4 were acting by an antigene mechanism, we measured relative hPR RNA levels using quantitative PCR. We observed diminished levels of hPR-B and hPR-A RNA, reflecting the reduced protein levels observed by Western analysis. Treatment with agPNAs did not change the levels of mRNAs encoding androgen receptor, GAPDH, or cyclophilin.

Time Dependence for agPNA, Antisense PNA, and siRNA Knock-Down Strategies. To further characterize agPNAs, we examined the efficiency of inhibition at varying times after transfection. AgPNAs P2 and P4 required more than 6 days before inhibition of hPR became apparent. By contrast, an siRNA targeted to hPR-B mRNA produced efficient inhibition after only 2 days. PNA P4 mm and mismatch-containing siRNA S2 mm did not inhibit expression of hPR at any time point.

siRNAs act through the RNA induced silencing complex (RISC) to cleave mRNA, whereas agPNAs would be expected to leave the pre-transfection pool of mRNA intact. Therefore, the observation that inhibition by agPNAs require more time than an siRNA may be explained by the fact that agPNAs do not block protein synthesis from preexisting mRNA. Alternatively, recognition of DNA by agPNAs is probably independent of cellular proteins, whereas recognition of mRNA by siRNAs is facilitated by RISC. Therefore, it is possible that recognition of chromosomal DNA in the nucleus may require more time for agPNAs because agPNAs cannot take advantage of highly evolved protein cofactors to locate target sequences.

Potency of Antigene Inhibition. To evaluate the efficiency of inhibiting hPR expression by agPNAs, we examined the dose response profile for agPNA P2 at concentrations ranging from 0 to 200 nM and compared it to the profiles for antisense PNA P7 targeted to hPR-B mRNA, and siRNA S2 targeted to hPR-B mRNA. PNA P2 inhibited expression of hPR at concentrations as low as 25 nM, a potency similar to that achieved by antisense PNA P7 or siRNA S2. Potencies of inhibition by agPNAs P1, P3, P4 were similar to P2. A mismatch analog of PNA P7, PNA P7 mm (Table 1), was tested as an additional control and did not inhibit hPR expression.

Relationship Between Expression of hPR-B and hPR-A. A striking feature of our data is the observation that agPNAs P1 and P2 inhibit expression of hPR-A, even though the target sites for P1 or P2 are approximately 760 bases upstream from the transcriptional start site for hPR-A. This finding indicates that binding of agPNAs P1 and P2 to the transcription start site of hPR-B exerts a powerful but unexpected effect on expression of hPR-A.

To characterize the linkage between hPR-B and hPR-A expression we graphed our data obtained using agPNAs P1 and P2. We compared this graph to data obtained using antisense PNA P7 targeted to the mRNA encoding hPR-B, siRNAs S1 and S2 targeted to hPR-B mRNA, and siRNAs S3 and S4 that were complementary to sequences found within both hPR-B and hPR-A MRNA.

The graphs describing inhibition by antisense PNA P7 and siRNAs S1 and S2 were similar. They revealed that the level of hPR-A inhibition increased abruptly as the level of hPR-B inhibition surpassed 90%. This abrupt transition is also apparent from visual inspection of the hPR-B and hPR-A protein levels. One explanation for the changing ratio of hPR-B and hPR-A is that a feedback mechanism exists to balance their expression. When hPR-B levels are dramatically reduced, the levels of hPR-A also decrease. The abrupt transition in isoform ratios has practical advantages because almost complete inhibition of hPR-B can be accompanied by nearly normal levels of hPR-A expression. This ability to selectively inhibit hPR-B allows investigation into the role of hPR-A in cells.

Demonstrating that subtle phenotypes are due to specific binding to the intended target is a key challenge for any gene silencing technology. The need to overcome this challenge makes the similar linkage profiles revealed by an siRNA and a antisense PNA especially significant. Antisense PNAs act by a different mechanism than do siRNAs, have dramatically different chemical properties, and would not be expected to produce similar off-target effects. Improper regulation of the ratio between hPR-B and hPR-A has been noted in some types of breast cancer (20), and the finding that two different RNA-directed knockdown methods produce the same phenotype reinforces the conclusion that coregulation of hPR-B and hPR-A represents a real biological feedback mechanism rather than an artifact.

In striking contrast to the exponential appearance of the graphs describing inhibition of hPR-B and hPR-A after treatment with anti hPR-B siRNAs or an antisense PNA, the graph relating the effects of treatment with agPNA P1 and P2 appears linear. Antigene PNAs that bind to the transcription start site for hPR-B also inhibit the initiation of transcription 760 bases away at the start site for hPR-A. It is possible that binding to the transcriptional start of hPR-B might disrupt important regulatory sequences for hPR-A. Alternatively, binding to the start site of hPR-B might interfere with RNA polymerase and obstruct its ability to scan the chromosome and locate the start site for hPR-A. Either explanation indicates inhibition of hPR-B and hPR-A would be directly linked. The finding that agPNAs targeting the hPR-B promoter produce different effects than do knock-down strategies that are directed against hPR-B mRNA is an example of how agPNAs can be used to obtain novel insights into gene expression that cannot be obtained using mRNA-directed strategies alone.

The graph of inhibition by agPNAs targeting hPR-B was similar to a graph describing inhibition by siRNAs S3 and S4 that targets a sequence within both hPR-B and hPR-A mRNA. A straightforward explanation for the linear relationship yielded by S3 and S4 is that the siRNAs bind to target sequences that are found within both isoforms causing the hPR-B and hPR-A mRNAs to be equally susceptible to RNAi.

Inhibition of hPR Expression Affects the Morphology of T47D Cells. During our routine visualization of cells under low magnification we noted an alteration in the morphology of T47D cells treated with agPNAs or siRNAs targeted against hPR. To further investigate this phenomenon we treated cells to inhibit hPR and examined living cells at higher magnification (63x) using confocal microscopy. Cells were untreated, transfected with mismatch agPNA P4 mm, transfected with agPNA P4, or transfected with siRNA S4 that targets hPR-B and hPR-A mRNA.

Untreated cells or cells treated with mismatch-containing PNA P4 mm exhibited a normal, flattened morphology. Normal morphology was also observed in cells treated with non-complementary PNA P5, noncomplementary siRNAs, or lipid alone. By contrast, cells treated with agPNA 4 or siRNA S4 exhibited a rounded shape and rose higher above the plate. Measurements indicated an increase in height of approximately two-fold. A similar increase in cell height was obtained using PNAs 1-3 and siRNA S3.

The observation that chromosome-directed agPNAs and mRNA-directed siRNAs produce the same cellular morphology, whereas various mismatch-containing or noncomplementary siRNAs and PNAs do not, supports the conclusion that the increased cell height is due to reduction of hPR expression. The similarity of results using siRNAs and agPNAs to investigate an unexpected phenotype further demonstrates once again the value of using knockdown strategies in tandem to validate novel observations.

As might be expected from the dramatic nature of the phenotype, rates of proliferation of cells treated with agPNAs, siRNAs, or antisense PNAs that were complementary to hPR were reduced relative to untreated cells or cells treated with noncomplementary control oligomers. However, the cells with reduced levels of hPR continued to adhere to cell culture dishes, divide, and could be maintained in culture indefinitely. Analysis of the cells using Fluorescence Assisted Flow Cytometry (FACS) showed no increase in apoptotic cells with reduced levels of hPR and no alteration in the distribution of cells within the cell cycle.

The increased cell height that we observe is similar to morphology recently noted in cells that have increased expression of ezrin, a protein that links actin and the membrane proteins and that may play an important role in tumor metastasis (27,28). This observation is relevant to our work because studies have linked ezrin with altered expression of hPR-B and hPR-A (29). To investigate possible involvement of ezrin in the observed phenotype we measured ezrin levels in cells treated with agPNAs P1-P4. Ezin RNA levels increased by up to 8-fold upon treatment with P1-P4, but were unchanged in cells treated with mismatch PNA P4 mm. Upregulation of ezrin upon reduction of hPR levels is consistent with the suggestion that hPR contributes to the maintenance of normal cytoskeletal structures by either directly or indirectly controlling ezrin levels.

Target Sequences for agPNAs. Our results indicate that PNAs can bind to chromosomal DNA at the transcription start site and inhibit gene expression.

EXAMPLE 2

Inhibition of Human Progesterone Receptor (hPR), Human Major Vault Protein (MVP), and Human Androgen Receptor (hAR) Expression by Double-Stranded Antigene RNA (agRNA) Oligomers Targeting the Open Complex in Chromosomal DNA We initially assayed agRNAs PR2, PR9, and PR24 (Table 2). Addition of these agRNAs to cells reduced protein and RNA levels. agRNAs PR9 and PR24 inhibited expression of both hPR-B and hPR-A even though the transcription start of hPR-A is approximately 760 bases away from the target site. The observed dependence of hPR-A levels on hPR-B expression is in agreement with results using antisense PNAs, antigene PNAs, and siRNAs that target hPR-B (see Example 1) and reflects a linkage between the expression of hPR-B and hPR-A. agRNAs that were not complementary to hPR did not affect hPR expression. Expression of actin, cyclophilin, and GADPH was unchanged. In all cases, agRNAs were introduced into T47D breast cancer cells by standard transfection methods using Oligofectamine.

A dose response profile for inhibition of hPR expression by agRNA 9 indicated an $IC_{50}$ value of ~2.5 nM. This $IC_{50}$ value was slightly better than those obtained using an anti-hPR-B siRNA (12 nM), an antisense PNA (12 nM), or antigene PNAs (25 nM). An agRNA containing just one mutation maintained some ability to inhibit gene expression, but all the other mutant agRNAs were inactive (see Table 2). Addition of 5-aza-dC or TSA had no effect on the inhibition that we observe, demonstrating that methylation is not necessary for inhibition of gene expression by agRNAs that target the transcription start site of hPR.

We then assayed agRNAs that targeted sequences throughout the −49 to +17 region (Table 2) at concentrations of 25 or 100 nM. Two groups of agRNAs PR7-10, PR13, and PR24, PR26 were the most active towards inhibition of hPR (Table 2). Each of these agRNAs partially overlaps the −9 to +2 region implicated in open complex formation.

agRNAs 11 and 25 were not inhibitors even though they were bracketed by potent inhibitors 10 and 12, or 24 and 26, though these six agRNAs had similar melting temperature values.

To determine whether agRNAs that were targeted to transcription start sites could inhibit the expression of other genes we designed agRNAs to be complementary to the start sites for human major vault protein (MVP) (Lange et al, 2000) and human androgen receptor (hAR) (Tilley et al, 1990). For MVP and hAR the agRNA targeting the −9 to +10 region inhibited gene expression. siRNAs that lacked complementarity to these targets were not inhibitors. As observed with hPR, agRNAs that were targeted to adjacent sequences within the AR promoter also silenced expression. These data indicate that the ability to target agRNAs to transcriptional start sites is a general phenomenon that can be applied to multiple genes.

Cells treated with hAR agRNAs grew as well as untreated control cells. Inhibition of hAR expression peaked at five days after transfection and had fully recovered by day 10. The recovery of expression is similar to time course data from standard mRNA-directed RNAs. The finding that expression is only transiently silenced further indicates that methylation is not occurring.

In Table 2, only one strand (5' to 3') of each agRNA is shown. Additionally, the agRNAs had 3'-dithymidine overhangs on each strand. Bases in MM1-MM4 that are mismatched (mm) relative to the target hPR gene are underlined. All experiments were repeated multiple times and values are averages. ni=no significant inhibition (measured values <20%).

TABLE 2

| ID | Sequence | | Target Site | % Inhibition 100 nM | 25 mM |
|---|---|---|---|---|---|
| Mismatch containing duplex RNAs based on PR9 | | | | | |
| MM1 | UGUCUGGGCAGUCCACAGC | (SEQ ID NO: 15) | | 91/67 | 75/53 |
| MM2 | UGUCUCGCCAGUCGACAGC | (SEQ ID NO: 16) | | ni/ni | — |
| MM3 | UCUCUGGGCAGUCCAGAGC | (SEQ ID NO: 17) | | ni/ni | — |
| MM4a | UCUCUCGCCAGUGCACACC | (SEQ ID NO: 18) | | ni/ni | — |
| MM4b | UCUCUCGCGAGUCCACAGC | (SEQ ID NO: 19) | | ni/ni | — |
| agRNAs that are fully complementary to hPR | | | | | |
| PR2 | CCAGUCCACAGCUGUCACU | (SEQ ID NO: 20) | -2/17 | 86/56 | 38/27 |
| PR6 | CUGGCCAGUCCACAGCUGU | (SEQ ID NO: 21) | -6/+13 | 71/26 | ni/ni |
| PR7 | UCUGGCCAGUCCACAGCUG | (SEQ ID NO: 22) | -7/+12 | 100/97 | 50/38 |
| PR8 | GUCUGGCCAGUCCACAGCU | (SEQ ID NO: 23) | -8/+11 | 88/67 | 73/67 |
| PR9 | UGUCUGGCCAGUCCACAGC | (SEQ ID NO: 24) | -9/+10 | 100/95 | 88/79 |
| PR10 | CUGUCUGGCCAGUCCACAG | (SEQ ID NO: 25) | -10/+9 | 100/99 | 55/50 |
| PR11 | GCUGUCUGGCCAGUCCACA | (SEQ ID NO: 26) | -11/+8 | 28/ni | ni/ni |
| PR12 | AGCUGUCUGGCCAGUCCAC | (SEQ ID NO: 27) | -12/+7 | 87/63 | 40/34 |
| PR13 | AAGCUGUCUGGCCAGUCCA | (SEQ ID NO: 28) | -13/+6 | 100/100 | 80/72 |
| PR14 | AAAGCUGUCUGGCCAGUCC | (SEQ ID NO: 29) | -14/+5 | ni/ni | ni/ni |
| PR19 | GUUAGAAAGCUGUCUGGCC | (SEQ ID NO: 30) | -19/-1 | ni/ni | ni/ni |
| PR22 | GUUGUUAGAAAGCUGUCUG | (SEQ ID NO: 31) | -22/-3 | ni/ni | ni/ni |
| PR23 | CGUUGUUAGAAAGCUGUCU | (SEQ ID NO: 32) | -23/-4 | 26/29 | ni/ni |
| PR24 | GCGUUGUUAGAAAGCUGUC | (SEQ ID NO: 33) | -24/-5 | 96/88 | 68/62 |
| PR25 | GGCGUUGUUAGAAAGCUGU | (SEQ ID NO: 34) | -25/-6 | ni/ni | ni/ni |
| PR26 | AGGCGUUGUUAGAAAGCUG | (SEQ ID NO: 35) | -26/-7 | 99/80 | 73/57 |
| PR29 | AGGAGGCGUUGUUAGAAAG | (SEQ ID NO: 36) | -29/-10 | 68/52 | 34/ni |
| PR34 | AGAGGAGGAGGCGUUGUUA | (SEQ ID NO: 37) | -34/-15 | ni/ni | ni/ni |
| PR39 | UCCCUAGAGGAGGAGGCGU | (SEQ ID NO: 38) | -39/-20 | 48/41 | ni/ni |
| PR44 | GGGCCUCCCUAGAGGAGGA | (SEQ ID NO: 39) | -44/-25 | ni/ni | ni/ni |
| PR49 | GGGCGGGGCCUCCCUAGAG | (SEQ ID NO: 40) | -49/-30 | 52/45 | 36/ni |
| DNA duplexes that are fully complementary to hPR | | | | | |
| DNA 9-1 | TGTCTGGCCAGTCCACAGCTT | (SEQ ID NO: 41) | -9/+10 | ni/ni | — |
| DNA 9-2 | TGTCTGGCCAGTCCACAGC | (SEQ ID NO: 42) | -9/+10 | ni/ni | — |
| agRNAs that are fully complementary to MVP | | | | | |
| MVP6 | CUCAGAUGGGGAACUCUCA | (SEQ ID NO: 43) | -6/+13 | 81 | |
| MVP9 | AGAUGGGGAACUCUCACCC | (SEQ ID NO: 44) | -9/+10 | 91 | |

TABLE 2-continued

| ID | Sequence | | Target Site | % Inhibition 100 nM | 25 mM |
|---|---|---|---|---|---|
| MVP14 | GGGAACUCUCACCCUGCCU | (SEQ ID NO: 45) | −14/+5 | ni | |
| MVPRNA | UAGGAGUCACCAUGGCAAC | (SEQ ID NO: 46) | | 99 | |
| MVRSCR | GUUGCCAUGUCCUAGUGAC | (SEQ ID NO: 47) | | ni | |
| agRNAs that are fully complementary to AR | | | | | |
| AR8A | CACCUCCCAGCGCCCCUC | (SEQ ID NO: 48) | −8/+9 | 100 | |
| AR9A | CCACCUCCCAGCGCCCCU | (SEQ ID NO: 49) | −9/+10 | 82 | |
| AR10A | UCCACCUCCCAGCGCCCC | (SEQ ID NO: 50) | −10/+9 | 34 | |
| AR11A | GGGGCGCUGGGAGGUGGAG | (SEQ ID NO: 51) | −11/+8 | 39 | |
| AR12A | UCUCCACCUCCCAGCGCCC | (SEQ ID NO: 52) | −12/+7 | ni | |
| AR13A | CUCUCCACCUCCCAGCGCC | (SEQ ID NO: 53) | −13/+6 | 100 | |
| AR14A | GCUCUCCACCUCCCAGCGC | (SEQ ID NO: 54) | −14/+5 | 92 | |

Several lines of evidence support the conclusion that the silencing we observe is due to recognition of chromosomal DNA: 1) agRNAs that are directed to transcription start sites of three different genes silence their respective target; 2) siRNAs that are not complementary to the target genes do not affect their expression; 3) agRNAs that target hPR reduce levels of hPR-B and hPR-A protein equally. The same outcome is obtained using antigene PNAs that target the same site. By contrast, siRNAs or antisense PNAs that target a site within hPR-B mRNA that is only 100 bases downstream from the target of siRNA PR9 can selectively inhibit hPR-B. The common outcome obtained using agPNAs and agRNAs indicates that they share a mechanism of action, i.e. blocking the transcription start site; 4) inhibition is dose dependent, potent, and reproducible.

A necessary function of the protein machinery involved in RNA-directed methylation is pairing of RNA with complementary DNA sequences. Our results indicate that these proteins can also pair RNA with sequences that are not within CpG islands.

Recognition of DNA sequences that are functionally important, like transcriptional start sites, disrupts critical interactions and leads to silencing independent of methylation. Our results lead to significant additional uses for agRNA as a tool for silencing gene expression in mammalian cells that are not possible with anti-mRNA siRNAs. For example, some genes are resistant to inhibition by standard mRNA-directed siRNAs, and thus transcription inhibition can instead be achieved by agRNAs. Also it can be difficult to successfully target every isoform of a gene with complex splicing. agRNAs have an advantage in that they abolish expression of each isoform equally.

EXAMPLE 3

Double-Stranded RNA Targeting the Open Complex of VEGF Inhibits Choroidal Neovascularization Laser-induced choroidal neovascularization (CNV) in the mouse is a model for age-related macular degeneration (AMD). In this example we use methodology adapted from Reich et al (2003) to demonstrate that dsRNAs targeting the open complex of VEGF can inhibit choroidal neovascularization in a mouse model of age-related macular degeneration.

The agRNAs are designed to target the open complex region of the mouse vascular endothelial growth factor (VEGF) gene. The promoter region of the mouse VEGF gene has been characterized (see e.g. Shima et al, 1996); the transcription start site is at position 1218 in the published sequence (GenBank Accession no. U41383.1). 19-mer agRNAs complementary to the template strand are synthesized and purified; exemplary agRNAs are shown in Table 3 (second strand and dinucleotide overhangs not shown).

TABLE 3 agRNAs that are fully complementary to mVEGF

| mV7 | GGUGAGAAGCGCAGAGGCU | (SEQ ID NO: 55) | −7/+12 |
|---|---|---|---|
| mV8 | CGGUGAGAAGCGCAGAGGC | (SEQ ID NO: 56) | −8/+11 |
| mV9 | CCGGUGAGAAGCGCAGAGG | (SEQ ID NO: 57) | −9/+10 |
| mV10 | ACCGGUGAGAAGCGCAGAG | (SEQ ID NO: 58) | −10/+9 |
| mV15 | CUGUUACCGGUGAGAAGCG | (SEQ ID NO: 59) | −15/+4 |
| mV19 | ACCGCUGUUACCGGUGAGA | (SEQ ID NO: 60) | −19/−1 |
| mV24 | CUUCCACCGCUGUUACCGG | (SEQ ID NO: 61) | −24/−6 |

Animal experiments are performed in accordance with institutional guidelines for the care and use of animals in research. Adult (8-15 week old) female C57B1/6 mice are anesthetized with avertin (2,2,2-tribromoethanol) and pupils are dilated with 1% tropicamide. Laser photocoagulation is performed bilaterally using a diode laser photocoagulator (IRIS Medical, Mountain View, Calif.) and slit lamp system with a cover slip as a contact lens. Laser photocoagulation (140 mW, 75 μm spot size, 0.1 s duration) is applied to the 8 and 10 o'clock positions in the right eye and 2 and 4 o'clock positions in the left eye, 2 to 3 disk diameters from the optic nerve. Since the rupture of Bruch's membrane is necessary to create significant CNV, bubble formation at the time of photocoagulation is used as an indication of the rupture of Bruch's membrane. Laser burns that do not induce a rupture in Bruch's membrane are excluded from the study. Lesions in which two laser spots become confluent are also excluded from the study.

agRNAs are delivered by subretinal injection to the retinal pigment epithelium (RPE) of mice 36 h after laser treatment to achieve ocular concentrations of 2 nM, 25 nM, 100 nM, and 250 nM. The areas of mV agRNA injection encompass all of the laser spots as well as untreated retina adjacent to the spots. Contralateral eyes receive control siRNA in which the mV siRNA is modified to have 4 mismatches of C to G or G to C. The mice are perfused with dextran-fluorescein 14 days after the laser treatment, the time of maximal neovascularization, and the areas of neovascularization are measured using digital image capture around the burn spots. The locations of the neovascular areas should exactly coincide with the sites initially exposed to laser. Neovascularization should not be observed in portions of the retina that have not been exposed to laser. agRNAs are determined to be effective inhibitors of VEGF transcription inferentially by detecting a resultant decrease in the area of neovascularization by at least 50% compared to control-treated spots, showing that agRNA targeting mVegf is capable of inhibiting CNV in the laser photocoagulation model.

EXAMPLE 4

Double-Stranded RNA Targeting the Open Complex of VEGF Inhibits Age-Related Macular Degeneration The promoter region of the human VEGF gene has been characterized (see e.g. Tischer et al, 1991). The transcription start site is at position 2363 in the published sequence (GenBank Accession no. AF095785.1). 19-mer agRNAs complementary to the template strand and targeting the open complex region (−50 to +25, where transcription start is +1) are prepared; exemplary agRNAs are shown in Table 3 (second strand and dinucleotide overhangs not shown).

TABLE 4

| agRNAs that are fully complementary to hVEGF | | | |
|---|---|---|---|
| hV2 | gaucgcggaggcuugggc | (SEQ ID NO: 62) | −2/+17 |
| hV6 | ggaggaucgcggaggcuug | (SEQ ID NO: 63) | −6/+13 |
| hV7 | gggaggaucgcggaggcuu | (SEQ ID NO: 64) | −7/+12 |
| hV8 | ggggaggaucgcggaggcu | (SEQ ID NO: 65) | −8/+11 |
| hV9 | cggggaggaucgcggaggc | (SEQ ID NO: 66) | −9/+10 |
| hV10 | gcggggaggaucgcggagg | (SEQ ID NO: 67) | −10/+9 |
| hV11 | agcggggaggaucgcggag | (SEQ ID NO: 68) | −11/+8 |
| hV12 | uagcggggaggaucgcgga | (SEQ ID NO: 69) | −12/+7 |
| hV13 | guagcggggaggaucgcgg | (SEQ ID NO: 70) | −13/+6 |
| hV14 | gguagcggggaggaucgcg | (SEQ ID NO: 71) | −14/+5 |
| hV15 | ugguagcggggaggaucgc | (SEQ ID NO: 72) | −15/+4 |
| hV19 | ucggcugguagcggggagg | (SEQ ID NO: 73) | −19/−1 |
| hV24 | aaaagucggcugguagcgg | (SEQ ID NO: 74) | −24/−6 |
| hV25 | uaaaagucggcugguagcg | (SEQ ID NO: 75) | −25/−7 |

TABLE 4-continued

| agRNAs that are fully complementary to hVEGF | | | |
|---|---|---|---|
| hV30 | uuuuuaaaagucggcuggu | (SEQ ID NO: 76) | −30/−12 |
| hV35 | uuuuuuuuuuaaaagucgg | (SEQ ID NO: 77) | −35/−17 |
| hV40 | ccccccuuuuuuuuuuaaaa | (SEQ ID NO: 78) | −40/−22 |
| hV45 | cgcccccccuuuuuuuuu | (SEQ ID NO: 79) | −45/−27 |
| hV49 | caugcgcccccccuuuuu | (SEQ ID NO: 80) | −49/−31 |

The effect of each agRNA on inhibition of VEGF gene transcription is initially determined in primary human umbilical vein cells (HUVECs). Resultant VEGF gene transcription inhibition is detected inferentially from decreases in cell proliferation and/or directly by measuring decreases in VEGF gene transcripts relative to controls. agRNA treatment resulting in at least 80% inhibition is evaluated in subsequent clinical studies.

In this example, the safety and efficacy of agRNA therapy is evaluated in a clinical study adapted from an ongoing clinical study by Gragoudas, et al. at the Massachusetts Eye and Ear Infirmary, and entitled Anti-angiogenic Therapy with Macugen for Patients with Choroidal Neovascularization Due to Age-Related Macular Degeneration (AMD). Patients eligible for this trial have primary subfoveal CNV that is not amenable to laser treatment; no other ocular disease which might compromise visual acuity; no prior participation in other studies of investigational drugs within 3 months of enrollment to treat AMD. Intravitreal injections of agRNA at dosages developed in animal studies (see e.g. Example III, supra) are given at six week intervals. Patients receive one of 3 doses of an agRNA or a sham injection every six weeks for 54 weeks. A subset of patients is randomized at the end of the period to continue injections for another 48 weeks.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

1. Kaihatsu, K., Janowski, B. A. & Corey D. R. (2004) Chem. Biol. 11, 749-758.
2. Knauert, M. P. & Glazer, P. M. (2001) Hum. Mol. Gen. 10, 2243-2251.
3. Besch et al. (2004) J. Mol. Biol. 341, 979-89.
4. Dervan P. B. & Edelson B. S. (2003) Curr. Opin. Struct. Biol. 13, 284-99.
5. Dudouet et al. (2003) Chem. Biol. 10, 859-67.
6. Kawasaki H. & Taira K. (2004) Nature 431, 211-7.
7. Morris K. V., Chan S. W., Jacobsen S. E. & Looney D. J. (2004) Science 305, 1289-92.
8. Nielsen, P. G., Egholm, M., Berg, R. H. & Buchardt, O. (1991) Science 254, 14971500.
9. Demidov, et al. (2001) ChemBiochem. 2, 133-139.
10. Larsen, H. J. & Nielsen, P. E. (1996) Nucl. Acids Res. 24, 458-463.

11. Mollegaard, et al. Proc. Natl. Acad. Sci. USA 91, 3892-3895.
12. Faruqi, et al. (1998) Proc. Natl. Acad. Sci. U S A. 95, 1398-403.
13. Bentin, T. & Nielsen, P. E. (1996) Biochemistry 35, 8863-8869.
14. Zhang, X., Ishihara, T. & Corey, D. R. (2000) Nucl. Acids Res. 28, 3332-3338.
15. Holstege, F. C., Fiedler, U. & Timmers, H. T. (1997) EMBO J. 16, 7468-80.
16. Kahl, B. F., Li, H. & Paule, M. R. (2000) J. Mol: Biol. 299, 75-89.
17. Milne, et al. (2000) Proc. Natl. Acad. Sci. USA 97, 3136-3141.
18. Kastner, et al. (1990) EMBO J. 9, 1603-14.
19. Misrahi, et al. (1993) Biochim. Biophys. Acta 1216, 289-92.
20. Conneely, et al. (2003) J. Mammary Gland Biol. Neoplasia 8, 205-14.
21. Kaihatsu, K., Huffinan, K. E. & Corey, D. R. (2004) Biochemistry 43, 14340-7.
22. Herbert, B-S., Pitts, A. E., Baker, S. I., Hamilton, S. E., Wright, W. E., Shay, J. W. & Corey, D. R. (1999) Proc. Natl. Acad. Sci. USA 96, 14726-1478.
23. Doyle D. F., Braasch D. A., Simmons, C. G., Janowski, B. A. & Corey, D. R. (2001) Biochemistry 40, 53-64.
24. Liu, Y., Braasch, D. A., Nulf, C. J. & Corey, D. R. (2004) Biochemistry 43, 19211927.
25. Nulf C. J. & Corey D. (2004) Nucl. Acids. Res. 32, 3792-3798.
26. Chomczynski, P. & Sacchi, N. (1987) Anal. Biochem. 162, 156-9.
27. Karmakar, S. & Das, C. (2004) J. Reprod. Imm. 64, 9-29.
28. Hunter, K. W. (2004) Trends Mol. Med. 10, 201-204.
29. McGowan, et al. (2003) Mol. Endocrinol. 31, 241-53.
30. Kuhn, et al. (1999) J. Mol. Biol. 286, 1337-45.
31. Stein, C. (1999) Nature Biotech. 17, 209
32. Jackson, A. L. & Linsley, P. S. (2004) Trends Genet. 20, 521-4.
Boffa et al (1996) J. Biol. Chem 271:13228-33
Braasch et al (2003) Biochemistry. 42:7967-75.
Czauderna et al (2003) Nucleic Acids Res. 31:2705-16.
Chan et al. (2004) Science 303, 1336.
Cutrona et al (2003) Cancer Res 63:6144-8.
Elbashir et al (2001) Nature. 411:494-8.
Elmen et al (2005) Nucleic Acids Res. 33:439-47
Haaima et al (1997) Nucleic Acids Res. 25:4639-43
Hahn, S. (2004) Nat Struct Mol Biol. 11:394-403.
Hassani et al (2004) J. Gene Med. 7:198-207
Kaihatsu et al (2003) Biochemistry. 42:13996-4003
Kaihatsu et al. (2004) Biochemistry 43, 14340-14347
Kawasaki et al (2005) Cell Cycle 4:e22-e28 (Epub ahead of print)
Lange et al (2000) Biochem Biophys Res Comm 278:125-133.
Matzke et al. (2004) Biochem. Biophys. Acta 1677, 129-141.
McMahon et al (2002) Life Sci 71:325-337
Motamedi et al. (2004) Cell 119, 789-802.
Nielsen (2004) Mol Biotechnol. 26:233-48
Paroo and Corey (2004) Trends Biotechnol. 22:390-4.
Reich et al (2003) Mol Vis. 9:210-6
Shima et al (1996) J. Biol Chem. 271:3877-83
Sigova et al. (2004) Genes Devel. 18, 2359-2367
Sugiyama et al. (2005) PNAS 102, 152-157.
Summerton and Weller (1997) Antisense Nucleic Acid Drug Dev.7:187-95
Takai and Jones (2002) Proc Natl Acad Sci U S A. 99:3740-5
Takai and Jones (2003) In Silico Biol. 3:235-40
Tischer et al (1991) J. Biol Chem. 266:11947-54
Tyler et al (1999) PNAS 96:7053-7058
Urban-Klein et al (2005) Gene Ther.12:461-6.
Wahlestedt et al (2000) Proc. Natl Acad. Sci. USA, 97:5633-5638.

What is claimed is:

1. A method of methylase-independently inhibiting transcription of a gene in a mammalian cell, the method comprising the steps of:
contacting the cell with a nucleic acid oligomer of 12-28 bases complementary to a partially single-stranded target genomic sequence of the gene, but not to an mRNA of the gene, whereby the transcription of the gene is subject to a resultant methylase-independent inhibition; and
detecting the resultant methylase-independent inhibition, wherein the oligomer is a double-stranded RNA, and the target genomic sequence is located between nucleotides −50 to +25 from the gene's transcription start site.

2. The method of claim 1 wherein the target genomic sequence is an open complex region located between nucleotides −30 to +17 from the transcription start site.

3. The method of claim 1 wherein the target genomic sequence is an open complex region located between nucleotides −15 to +10 from the transcription start site.

4. The method of claim 1 wherein the target genomic sequence includes nucleotides −9 to +2 from the transcription start site.

5. The method of claim 1 wherein the target genomic sequence includes the transcription start site.

6. The method of claim 1 wherein the target genomic sequence is not within a CpG 7. The method of claim 1 wherein the target genomic sequence does not include a CG dinucleotide.

8. The method of claim 1 wherein the oligomer is a double-stranded RNA of 8-25 bases.

9. The method of claim 1, wherein the oligomer comprises a nucleotide having a 2' chemical modification.

10. The method of claim 1, wherein the oligomer comprises a serum stability-enhancing chemical modification selected from the group consisting of a phosphorothioate internucleotide linkage, a 2'-0-methyl ribonucleotide, a 2'-deoxy-2'-fluoro ribonucleotide, a 2'-deoxy ribonucleotide, a universal base nucleotide, a 5-C-methyl nucleotide, an inverted deoxyabasic residue incorporation, and a locked nucleic acid.

11. The method of claim 1 wherein the cell is a cultured cell in vitro.

12. The method of claim 1 wherein the cell is in situ in a host.

13. The method of claim 1 wherein the cell is a cultured cell in vitro, the oligomer is a double-stranded RNA of 18-25 bases, and the cell is contacted with a composition comprising the oligomer and a cationic lipid.

14. The method of claim 1 wherein the cell is in situ in a host, the oligomer is a double-stranded RNA of 18-25 bases, and the cell is contacted with a composition consisting essentially of the oligomer.

15. The method of claim 1 wherein the contacting step is free of viral transduction.

16. The method of claim 1 wherein the contacting step is free of viral transduction, and the cell is contacted with a composition consisting essentially of the oligomer.

17. The method of claim 1 wherein the contacting step is free of viral transduction, and the inhibition is at least 90%.

18. The method of claim 1 wherein the oligomer is a double-stranded RNA of 18-25 bases, the inhibition is at least 90%, and a single sequence of the gene is targeted.

19. The method of claim 1 wherein the contacting step is free of viral transduction, and the oligomer is not attached to a nuclear localization peptide.

20. The method of claim 1 wherein the cell is contacted with a 1-100 nanomolar concentration of the oligomer.

* * * * *

UNITED STATES PATENT AND TRADEMARK OFFICE
CERTIFICATE OF CORRECTION

| | | |
|---|---|---|
| PATENT NO. | : 8,999,943 B2 | Page 1 of 1 |
| APPLICATION NO. | : 11/376483 | |
| DATED | : April 7, 2015 | |
| INVENTOR(S) | : Corey et al. | |

It is certified that error appears in the above-identified patent and that said Letters Patent is hereby corrected as shown below:

On the title page, item (57) line 3, after "complementary", delete "for" and insert --to--.

In the Claims

Claim 6, column 46, line 65, after "CpG", insert --island.--.

Claim 8, column 47, line 2, delete "8" and insert --18-- therefor.

Signed and Sealed this
Fifteenth Day of September, 2015

Michelle K. Lee
*Director of the United States Patent and Trademark Office*